US010114807B2

(12) United States Patent
Esibov et al.

(10) Patent No.: US 10,114,807 B2
(45) Date of Patent: Oct. 30, 2018

(54) AUTOMATICALLY EVALUATING LIKELY ACCURACY OF EVENT ANNOTATIONS IN FIELD DATA

(71) Applicant: Physio-Control, Inc., Redmond, WA (US)

(72) Inventors: Alexander Esibov, Redmond, WA (US); Isabelle Banville, Newcastle, WA (US); Robert Marx, Kent, WA (US); Fred Chapman, Newcastle, WA (US); Randy Merry, Woodinville, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 193 days.

(21) Appl. No.: 13/964,811

(22) Filed: Aug. 12, 2013

(65) Prior Publication Data
US 2014/0047314 A1   Feb. 13, 2014

Related U.S. Application Data

(60) Provisional application No. 61/682,170, filed on Aug. 10, 2012.

(51) Int. Cl.
*G06F 17/20* (2006.01)
*G06F 17/24* (2006.01)
*A61N 1/39* (2006.01)
*G06F 17/27* (2006.01)

(52) U.S. Cl.
CPC ....... *G06F 17/241* (2013.01); *A61N 1/39044* (2017.08); *G06F 17/27* (2013.01)

(58) Field of Classification Search
CPC ............... G06F 17/241; G06F 3/04883; G06F 19/3406; G06Q 10/10; A61N 1/39–1/3993
See application file for complete search history.

(56) References Cited

U.S. PATENT DOCUMENTS

| 5,090,418 A * | 2/1992 | Squires ............... A61B 5/0464 600/515 |
| 5,891,048 A * | 4/1999 | Nigam ................. A61N 1/3704 128/901 |
| 5,941,829 A * | 8/1999 | Saltzstein ........... A61B 5/0006 128/904 |
| 2006/0173501 A1 * | 8/2006 | Stickney ............... A61B 5/046 607/5 |

(Continued)

*Primary Examiner* — Keith Bloomquist
*Assistant Examiner* — Shahid Khan
(74) *Attorney, Agent, or Firm* — Lane Powell PC (57) ABSTRACT

Embodiments operate in contexts where field data have been generated from a field event, and annotations have been generated from the field data, which purport to identify events within the field data, such as CPR compressions and ventilations. Metrics are generated from the annotations, which are used in training. In such contexts, a grade may be assigned that reflects how well the annotations meet one or more accuracy criteria. The grade may be used in a number of ways. Reviewers may opt to disregard field data and metrics that have a low grade. Expert annotators may be guided as to precisely which annotations to revise, saving time. A low grade may decide that the results are not emailed to reviewers, but to annotators. A learning medical device can use the grade internally to adjust its own internal parameters so as to improve its annotating algorithms.

23 Claims, 10 Drawing Sheets

METHODS (56) References Cited

U.S. PATENT DOCUMENTS

| | | | |
|---|---|---|---|
| 2007/0197929 A1* | 8/2007 | Porath | A61B 5/0422 600/523 |
| 2012/0022350 A1* | 1/2012 | Teixeira | A61B 5/0205 600/324 |
| 2013/0346356 A1* | 12/2013 | Welinder | G06F 17/30598 706/52 |

* cited by examiner

FIG. 1

SAMPLE FIELD DATA
(CHEST COMPRESSION VALUES)

FIG. 2 (PRIOR ART)

SAMPLE FIELD DATA WITH ANNOTATIONS
(IDENTIFIED CPR COMPRESSIONS)

FIG. 5  *GRADE AS A SCORE*

FIG. 6  *GRADE IN BAND*

*SAMPLE INITIAL DISPLAY OF METRICS & GRADES FOR UNDERLYING ANNOTATIONS*

FIG. 7A

| Incident ID | CPR ratio % | Compr. ratio % | Compr /min | Grade for annotations |
|---|---|---|---|---|
| (Event 01) | ... | ... | ... | A - Proficient |
| (Event 02) | ... | ... | ... | B - Acceptable |
| (Event 03) | ... | ... | ... | A - Proficient |
| (Event 04) | ... | ... | ... | A - Proficient |
| (Event 05) | ... | ... | ... | A - Proficient |
| (Event 06) | ... | ... | ... | A - Proficient |
| (Event 07) | ... | ... | ... | B - Acceptable |
| (Event 08) | ... | ... | ... | A - Proficient |
| (Event 09) | ... | ... | ... | A - Proficient |
| (Event 10) | ... | ... | ... | A - Proficient |

*SAMPLE DISPLAY OF UPDATED METRICS & GRADES AFTER ADJUSTING UNDERLYING ANNOTATIONS*

*EMBODIMENTS*

FIG. 10

AUTOMATICALLY EVALUATING LIKELY ACCURACY OF EVENT ANNOTATIONS IN FIELD DATA

CROSS REFERENCE TO RELATED PATENT APPLICATIONS

This patent application claims priority from U.S. Provisional Patent Application Ser. No. 61/682,170, filed on Aug. 10, 2012, titled: "A USER-COMPATIBLE INTERFACE FOR EASILY IDENTIFYING CPR DATA FILES NEEDING DIFFERENT ATTENTION", the disclosure of which is hereby incorporated by reference for all purposes.

BACKGROUND

In certain types of medical emergencies, Cardio Pulmonary Resuscitation (CPR) needs to be delivered to a patient. CPR includes repeatedly compressing the chest of the patient, to cause their blood to circulate some. CPR also includes delivering rescue breaths to the patient, which are also known as ventilations. Delivering the compressions and the ventilations should be performed according to appropriate protocols that specify repetitions, repetition rates, and so on.

Professional rescuers are trained in CPR. However, it is understandably difficult to apply the training perfectly in all real life circumstances. Accordingly, there is an effort to review what happened in the field, and learn from it. To this end, some medical devices capture enough data in the field, so that the application of CPR can be discerned. More particularly, periodically occurring events in the field data, such as chest compressions and ventilations, can be identified and therefore marked by generating appropriate annotations. The annotations can also be called markers. Then metrics can be computed from the annotations or markers, and reviewed by the rescuers.

A problem happens with the annotations, which are typically generated by software. The task of identifying events within the field data is complex, and sometimes it is not performed correctly. At those times, the generated annotations do not correspond accurately to the events, and the resulting metrics computed from such annotations are unreliable. It is possible for a skilled annotator to adjust the annotations generated by the software and fix the problem, but that is time consuming. And time and effort are wasted because the skilled annotator does not know whether to even invest the time to verify that the annotations in a set of field data, to determine whether they are correct or need adjusting.

BRIEF SUMMARY

The present description gives instances of devices, systems, computers, software and methods, the use of which may help overcome problems and limitations of the prior art.

Some embodiments operate in contexts where field data have been generated from a field event, and annotations have been generated from the field data, which purport to identify events within the field data. Metrics are generated from the annotations, which are used in training. In such contexts, a grade may be assigned that reflects how well the annotations meet one or more accuracy criteria.

Advantages of the invention arise from the versatility of how the grade may be used. In a number of embodiments, a user signal may be output that encodes the grade. Once the grade is made available, reviewers may opt to disregard field data that has a low grade. Alternately, an expert annotator may be guided precisely as to which annotations to revise, saving time. Or, the expert annotator may override the grade, judging that the metrics are duly extreme, as the field data was indeed unusual.

In a number of embodiments, the grade is made available to computers internally. In some embodiments, the grade may determine to which network destination to send a data file that includes the field data. In some embodiments, the grade may be used to adjust the function of annotating itself, in a learning mode.

Another advantage over the prior art is that rescuers do not become trained on unhelpful or wrong field data and metrics. In addition, reviewers save time upon knowing which data files to address, and which not.

These and other features and advantages of this description will become more readily apparent from the following Detailed Description, which proceeds with reference to the drawings, in which:

DETAILED DESCRIPTION

As has been mentioned, the present description is about ways for assigning grades to annotations in field data, and using the grades to help with the review process. Embodiments are now described in more detail.

Figure 1:
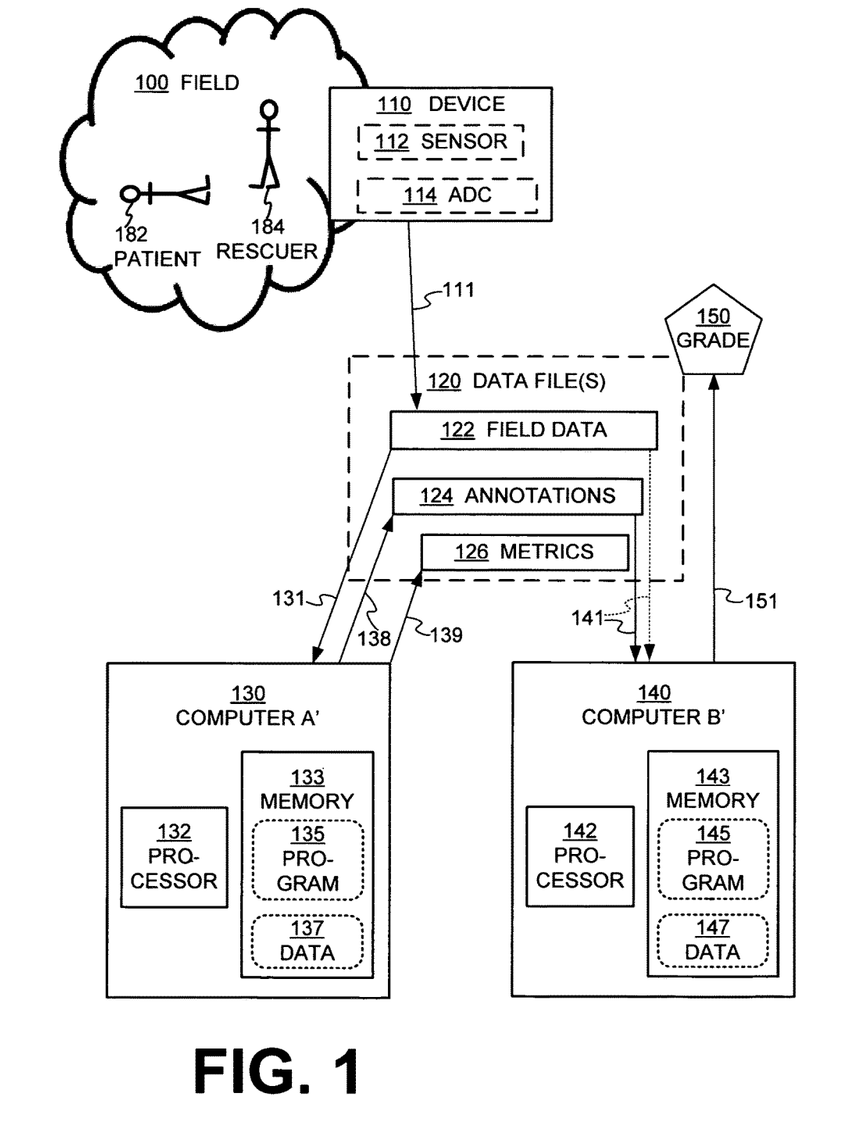
FIG. 1 is a conceptual diagram for describing managing data according to embodiments of the invention.

Referring to FIG. 1, managing data according to embodiments is described. FIG. 1 shows a field 100 where an event could be happening, a device 110, a Computer A' 130 and a Computer B' 140. However, FIG. 1 does not speak to the location of Computer A' 130 and Computer B' 140 relative to field 100; rather, FIG. 1 is designed to illustrate some embodiments of managing data between them.

An event may take place in field 100, where a patient 182 is tended to by a rescuer 184. Device 110 may also be used in the event, for example by rescuer 184. Device 110 may be a medical device that has components for sensing parameters of patient 182, and/or administering a medical treatment. For example, device 110 may be a monitor-defibrillator, a CPR machine, a CPR-assist device, and so on. In addition, as will be seen later in this document, device 110 may also have components and functionalities of Computer A' 130 and/or Computer B' 140, such as for running programs, interfacing with users, and so on.

Device 110 has ways of capturing field data 122 from the event in field 100. Field data 122 may be from patient 182. Accordingly, device 110 may include one or more sensing components, such as a sensor 112. Sensor 112 may sense an impedance of patient 182, or an ECG of patient 182, for example by using signals sensed between defibrillation electrodes attached to the skin of patient 182. Alternately, sensor 112 may sense a height of the chest of patient 182, for example by being a position detector, an accelerometer, and so on. Examples of a position detector are shown in US Patent Application No. 2010/0022904, published on Jan. 28, 2010, and which is incorporated herein by reference. In some embodiments, two devices may be employed, alone or in combination. A CPR machine or CPR feedback device could have sensor 112, and communicate its field data to a monitor-defibrillator in field 100. Device 110 may also include components for processing an output of sensor 112. A sample such component is an optional Analog-to-Digital Converter ADC 114.

Device 110 may keep field data 122, or export it according to an arrow 111. Exporting field data 122 means transmitting it to a receiving device over a communication network such as the internet. The transmission can have a leg that is wireless, and so on. The receiving device may be in the cloud, and can be a server, a desktop computer, a laptop computer, a tablet computer, a smartphone, and so on. Device 110 may have a suitable transmitter, and appropriate circuitry for transmitting. Similarly, Computer A' 130 and Computer B' 140 may communicate with the receiving device, if they are not part of device 110. Alternately, Computer A' 130 and/or Computer B' 140 may be the receiving devices, could be in the cloud, and so on.

Whether field data 122 is exported, or retained within device 110 for further processing, field data 122 may be organized as part of one or more data files 120. An example of field data 122 is now described.

Figure 2:
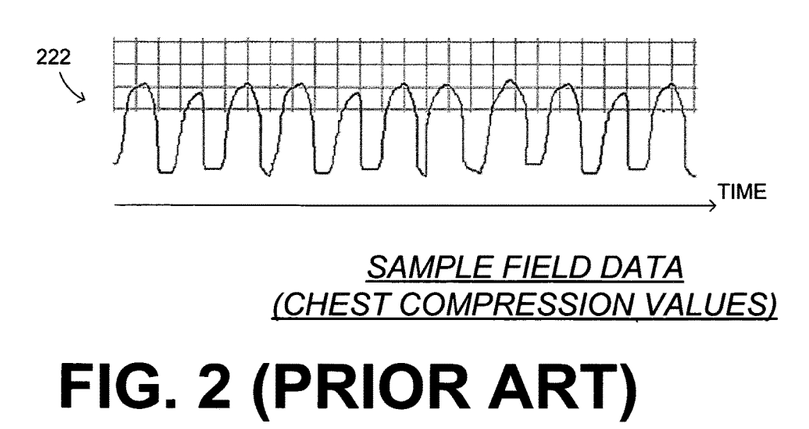
FIG. 2 is a diagram showing sample field data in the prior art.

FIG. 2 is a diagram showing sample field data 222 in the prior art. Field data 222 could be field data 122 of FIG. 1. Field data 222 is arranged along a time dimension and, in this example, it is a waveform that corresponds to chest compressions of a patient. This is the kind of waveform that can be delivered when sensor 112 includes a CPR machine, a CPR-assist device, and so on. This is also the kind of waveform that may be derived by processing appropriately the ECG and/or impedance signals of patient 182. The patient's impedance changes in response to chest compressions, but noise should be removed from the impedance signal, for the chest compressions to be identified. Some ways of processing such signals are taught in Physio-Control US Patent Application No. 2011/0082379, published on Apr. 7, 2011, and which is incorporated herein by reference, in addition, patient waveforms derived by the ECG or impedance signals may be accurate as to the timing of compressions, but not necessarily as to the depth.

Returning to FIG. 1, Computer A' 130 receives field data 122, generates annotations 124, and computes metrics 126. Examples of computing metrics can be found in Physio-Control's U.S. Pat. No. 8,060,199, titled "CPR TIME INDICATOR FOB A DEFIBRILLATOR DATA MANAGEMENT SYSTEM", which is hereby incorporated by reference. Annotations 124 and/or metrics 126 may also be retained as part of data file(s) 120.

If Computer A' 130 is not within device 110, field data 122 is received according to arrow 131, annotations 124 are transmitted per arrow 138, and metrics 126 are transmitted per arrow 139. Again, transmissions per these arrows can be across links in a communication network. Plus, if transmission is from device 110 directly to Computer A' 130, then there is no "stop" where arrow 111 ends and arrow 131 begins, and so on with the possibilities of combinations of other arrows.

Computer A' 130 and computer B' 140 are now described in more detail. They could be two separate computers, or a single one as described later in this document. Each may be a system. They may have components that are commonly known for computers, for example ports for receiving and transmitting data such as via the arrows of FIG. 1. Of course, the ports receive and transmit, the signals that encode the data, and so on. The components may also include user interfaces, which operate to interact with human operators. The user interfaces may include keyboards and output devices such as speakers, display screens, and so on. The output devices may emit human perceptible indications for the users, such as sounds, lights, images and so on.

Computer A' 130 and Computer B' 140, and possibly also device 110, perform functions, processes and/or methods, as described in this document. The functions, processes and/or methods may be implemented by one or more devices that include logic circuitry. These devices can be standalone devices or computer, such as a general purpose computer, or part of a device that has one or more additional functions, such as for medical purposes. The logic circuitry may include respective processors 132, 142 that may be programmable for a general purpose, or dedicated, such as microcontrollers, microprocessors, Digital Signal Processors (DSPs), etc. Processors 132, 142 may cause various signals to be outputted, such as a user signal that encodes data. An output device of the user interface, responsive to receiving the user signal, may output a human perceptible indication that conveys to the user the encoded data.

The logic circuitry may also include storage media, such as memories 133, 143, Such media include but are not limited to read only memory (ROM); random access memory (RAM); magnetic disk storage media: optical storage media; smart cards, flash memory devices, etc. Such a storage medium can be a non-transitory computer-readable medium. These storage media, individually or in combination with others, can have stored thereon programs 135, 145, which the respective processors 132, 142 may be able to read, and execute. More particularly, programs 135, 145 can include instructions in the form of code, which respective processors 132, 142 may be able to execute upon reading. Executing is performed by physical manipulations of physical quantities, and may result in the functions, processes and/or methods to be performed. In addition, these storage media 133, 143 may store respectively data 137, 147.

In the arrangement of FIG. 1, Computer A' 130 can thus be a remote server that performs the heavy lifting of processing. When completed, metrics 126 can be delivered to the place of work of rescuer 184, for later review. The sooner the review after the event in field 100, the more feedback and learning will be retained.

In other embodiments, the metrics are computed in view of annotations 124, but from a different device than the computer that generated the annotations. For example, the annotations may be furnished from device 110; they may have been generated by device 110, or received by device 110 from yet another device. An example of the annotations in the prior art is now described.

Figure 3:
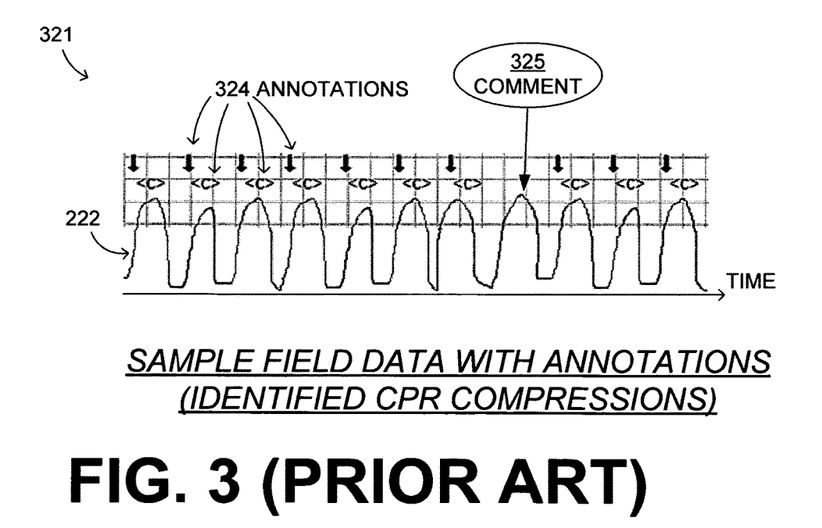
FIG. 3 is a diagram showing the sample field data of FIG. 2, plus superimposed annotations generated as in the prior art.

FIG. 3 is a diagram 321 along a time axis. Diagram 321 includes field data 222 of FIG. 2, plus superimposed annotations 324, which are generated as in the prior art. Annotations 324 include vertical arrows, which indicate times of occurrence of compressions of the patient's chest at specific points with respect to the time axis. The times could he just a selected moment, that represents the entire pattern of compression and release. In addition, the marker "<c>" is written, to visually aid the reviewer, or the annotator who might want to make adjustments.

It is not always easy for a computer to generate annotations 324. Some recognition tasks are easier for humans than are for computers. For example, per comment 325, no annotation is assigned for an entire pattern of a chest compression and release. That pattern has been missed; it has not been identified, it has not been counted, and it will cause the metrics to be unreliable. This is the kind of problem that a skilled annotator would have to fix, if they knew about it, and if they had the time.

Returning to FIG. 1, Computer B' 140 may receive annotations 124, and optionally also field data 122, for example according to arrows 141. Then Computer B' 140 may assign a grade 150 according to arrow 151. Generally, grade 150 is about the accuracy of annotations 124 with respect to field data 122. Operations of Computer B' 140 are now described in more detail in terms of its algorithms and methods.

The methods and algorithms described below are not necessarily inherently associated with any particular logic device or other apparatus, such as only Computer A' 130, or only Computer B' 140. Rather, they are advantageously implemented by programs for use by a computing machine, such as a general-purpose computer, a special purpose computer, a microprocessor, etc.

Often, for the sake of convenience only, it is preferred to implement, and describe a program as various interconnected distinct software modules or features, individually and collectively also known as software. This is not necessary, however, and there may be cases where modules are equivalently aggregated into a single program, even with unclear boundaries, in some instances, software is combined with hardware, in a mix called firmware.

This detailed description includes flowcharts, display images, algorithms, and symbolic representations of program operations within at least one computer readable medium. An economy is achieved in that a single set of flowcharts is used to describe both programs, and also methods. So, while flowcharts described methods in terms of boxes, they also concurrently describe programs. A method is now described.

Figure 4:
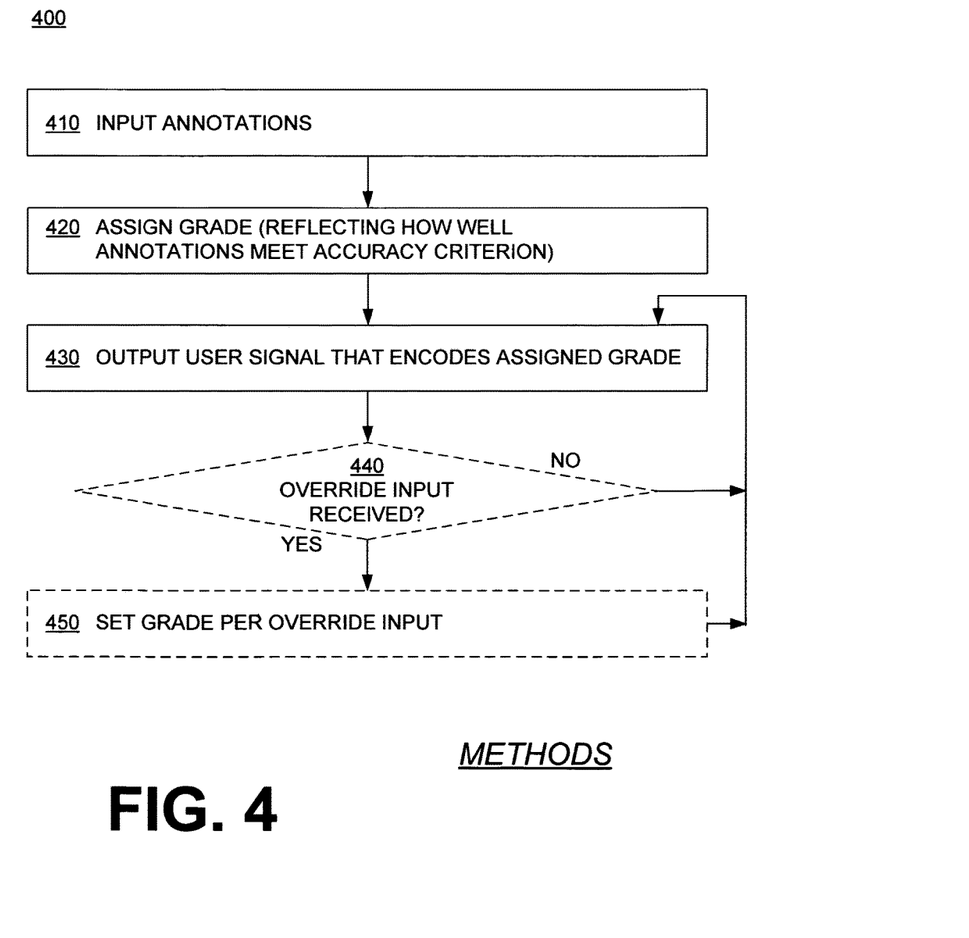
FIG. 4 is a flowchart for illustrating methods according to embodiments of the invention.

FIG. 4 shows a flowchart 400 for describing methods according to embodiments. The methods of flowchart 400 may also be practiced by embodiments such as Computer B' 140.

According to an operation 410, annotations may be input. The annotations may have been previously generated from field data, which could have been derived from a CPR session. The annotations could optionally be organised in one or more data files 120. Inputting may be from another device, or from the same device. The annotations may purport to identify events within the field data. The field data could be arranged along a time dimension, and the annotations could include events identified as occurring in sequence, at different times along the time dimension. The events could be repeating patterns within the field data. For example, if the field data has been derived from a CPR session, the events could be chest compressions or ventilations within the CPR session.

According to a next operation 420, a grade is assigned, such as grade 150 of FIG. 1. The grade is one of at least two possible grades, and it may reflect how well the annotations meet one or more accuracy criteria. Examples of more detailed accuracy criteria are presented later in this document. At the high level, the grade can be assigned in a number of ways, and two examples are described.

Figure 5:
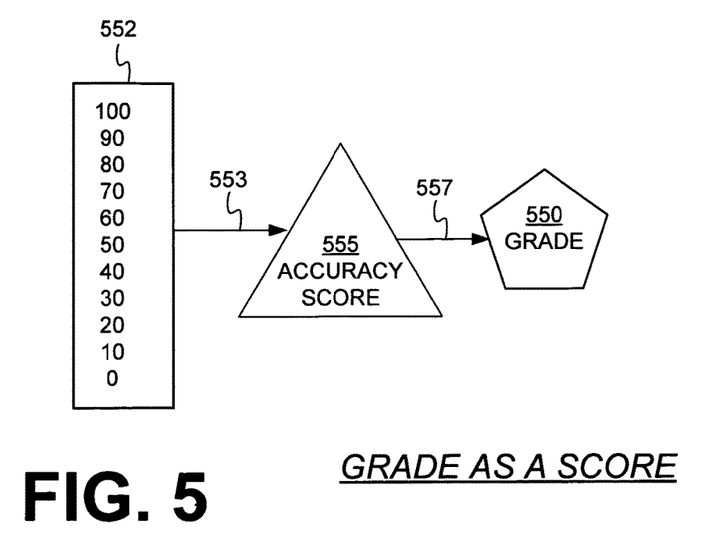
FIG. 5 is a conceptual diagram for illustrating how a grade is assigned according to embodiments.

Referring to FIG. 5, an accuracy score 555 can be computed by computation 553. Computation 553 can give a value for accuracy score 555 out of a set 552 of many possible values. In the example of FIG. 5, the possible values are designed to range from 0 to 100. Computation 553 can be from one or more statistics of the annotations, and the value of accuracy score 555 would then ultimately be a measure for how well the one or more statistics meet the one or more accuracy criteria. Then, grade 550 can be derived from accuracy score 555 according to an operation 557, or it can be accuracy score 555 itself. A challenge with this approach is that merely a number for grade 550 might not be meaningful for the reviewer. Rather, the reviewer may prefer the grade to convey a judgment, or an instruction. That is not a problem in the other example below.

Figure 6:
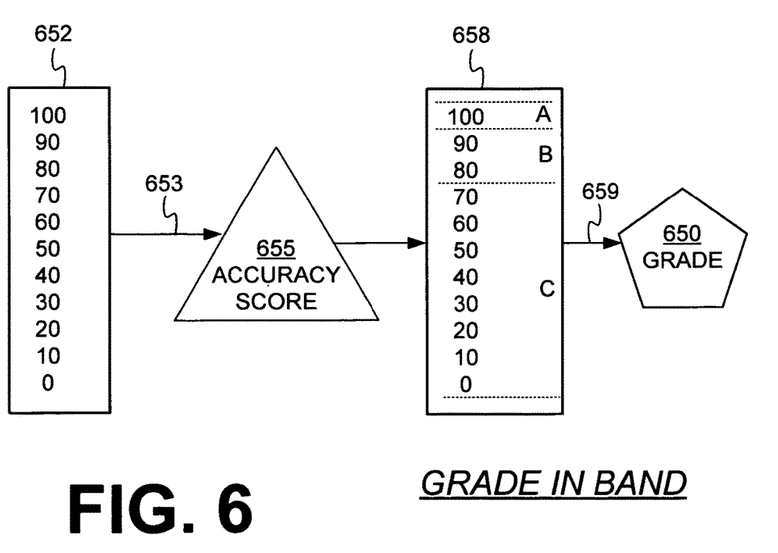
FIG. 6 is a conceptual diagram for illustrating how a grade is assigned according to other embodiments.

Referring to FIG. 6, an accuracy score 655 can be computed by computation 653. Computation 653 can give a value for accuracy score 655 out of a set 652 of many possible values, as in the example of FIG. 5. In addition, accuracy score 655 may be checked against a set 658 of possible bands, to see which of the bands it fits in. Then grade 650 is looked up according to an operation 659 from the band that accuracy score 655 fits in. In the example of FIG. 6, there are three bands, and grade 650 is one of three possible letter grades A, B and C. Moreover, each of these letter grades can include a judgment, and an instruction, as will be described below.

Returning to FIG. 4, according to a next operation 430, a user signal is output that encodes the grade. This is similar to operation 151 of FIG. 1. It should be remembered that, when an output device of the user interface receives the user signal, it can output a human perceptible indication that conveys the encoded grade. Since the grades can be different, the human perceptible indications can be correspondingly different. In some embodiments, the grade is encoded to be heard with a different sound than sounds of the other possible grades. In some embodiments, the grade is encoded to appear in a different color or image than colors or images of the other possible grades.

In some embodiments, the user signal also encodes metrics 126 that are computed from annotations 124. This encoding is in association with grade 150. As such, a reviewer could make an association of which metrics are associated with which grade. An example is now described.

Figure 7A:
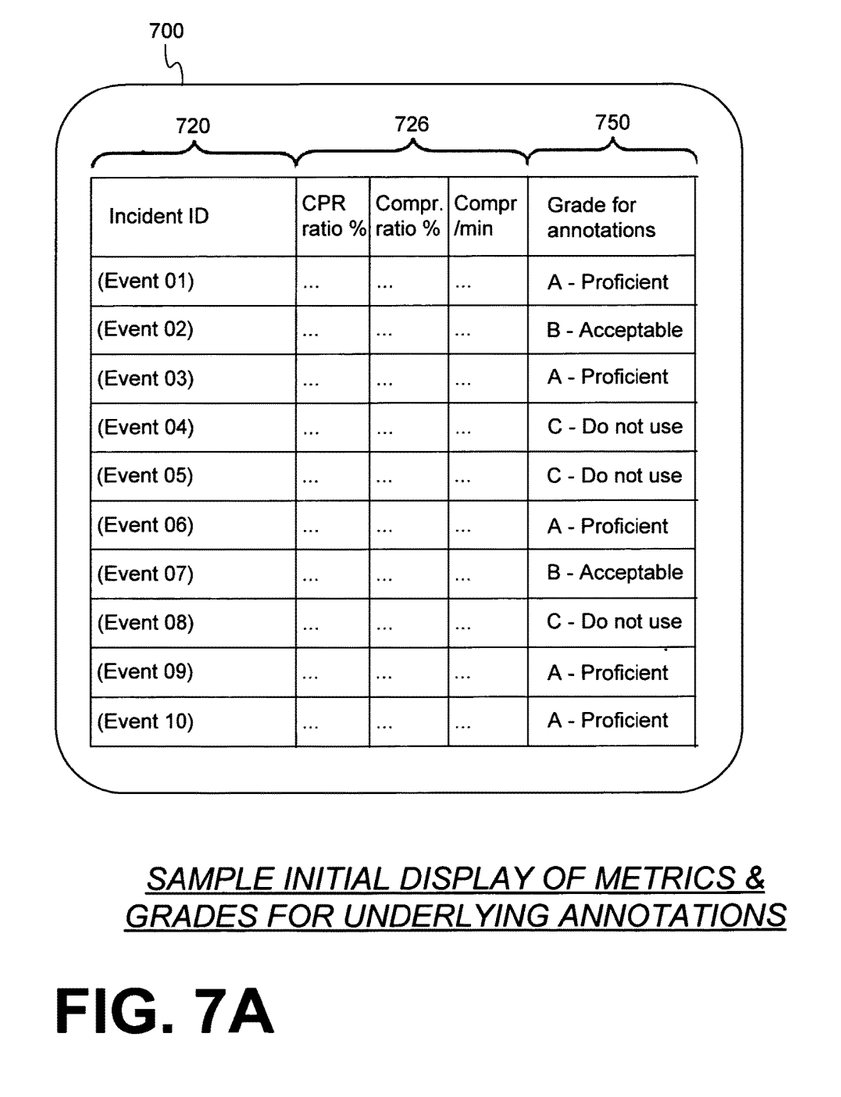
FIG. 7A is a diagram showing a sample screen displaying a sample embodiment of how assigned grades can be conveyed initially.

FIG. 7A is a diagram showing a sample screen 700. Screen 700 displays a sample embodiment of how assigned grades 750 can be conveyed initially. It will be recognised that the grades are letter grades, such as from set 658 of bands in FIG. 6. In addition, each letter grade is followed by an instruction. Grades 750 are shown vertically, one for each row. Each row contains information about a data file 720, which could be the same as data file 120. The information could be the event ID, the type of device 110 used, and so on. Each row could further contain metrics 726 about the event. In FIG. 7A, metrics 776 are shown for CPR chest compressions, but that is only for example. Metrics, and grades, could be shown also for ventilations, and so on.

An advantage of the invention arises from the fact that metrics 726 are shown together with grades 750. Since grades 750 are a measure of confidence in the annotations that created metrics 726, grades 750 thus are also a measure of confidence in metrics 726. Accordingly, the reviewer knows immediately which rows of metrics 726 to trust, and which not. Those with grades A and B can be trusted more than those graded C. In addition, as per the above, the colors could be different—grades A could be colored green, B yellow and C red.

Returning to FIG. 4, in some embodiments, after operation 430, execution returns to operation 410. In other words, operation 410 is repeated by inputting adjusted annotations. The annotations that were input the first time may have been generated by a computer, such as Computer A' 130. At this time that operation 410 is repeated, however, the inputted annotations may have been adjusted, by a person who is also reviewing the field data. According to operation 420, an adjusted grade may be assigned, and according to operation 430, a user signal may he output that encodes the adjusted grade. An example is now described.

Figure 7B:
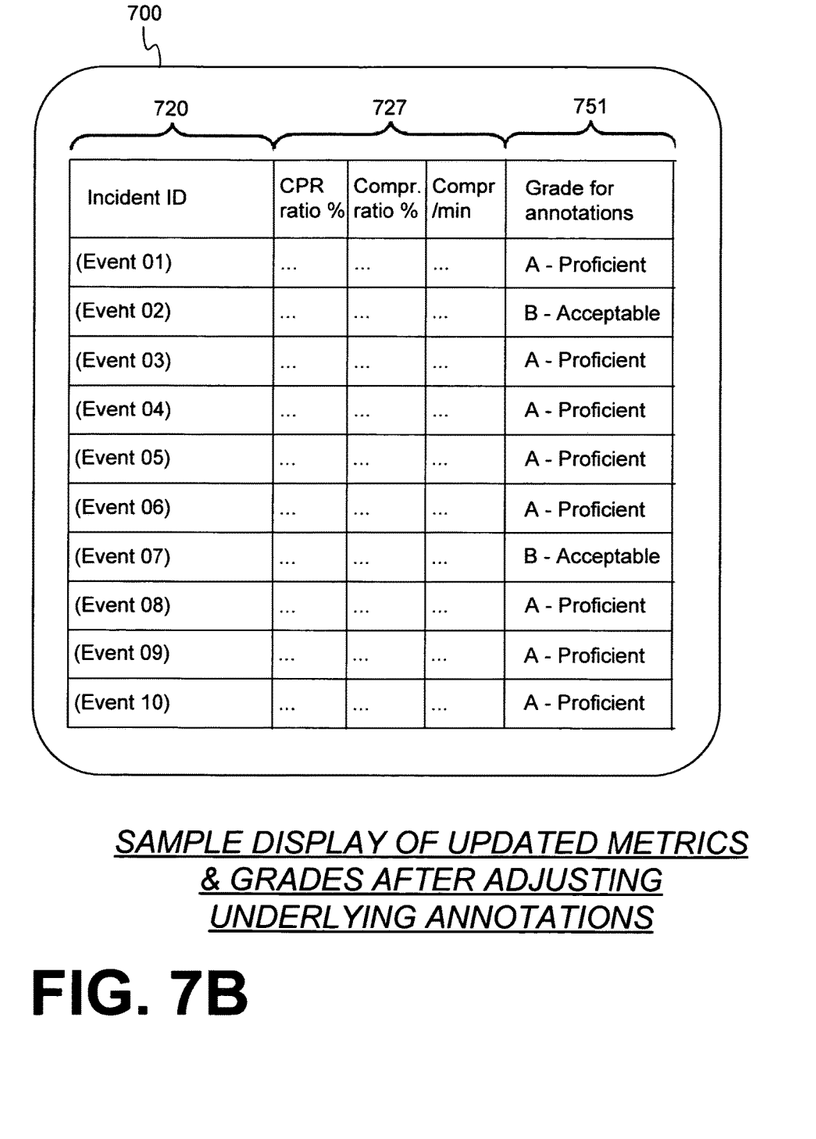
FIG. 7B is a diagram showing the sample screen of FIG. 7A, further after an expect annotator has adjusted some of the annotations as guided by what is displayed in the screen of FIG. 7A.

FIG. 7B is a diagram showing again sample screen 700 of FIG. 7A. That is, however, after an expert annotator has adjusted some of the underlying annotations. The annotator may have been guided by what is displayed in the screen of FIG. 7A. The annotator may have adjusted the annotations of only the rows with a grade of C, resulting in dynamically updated metrics 727 and updated grades 751. Because grades 750 were determined and displayed in screen 700 of FIG. 7A, the annotator has saved valuable time by not dealing with the rows that were acceptable in the first place. Given circumstances, the annotator may then also want to review and adjust those graded B.

Returning to FIG. 4, an optional operation 440 may take place after operation 430. More particularly, it may be inquired whether an override input has been received. Such may be received by the expert annotator after reviewing field data 122, and who may have determined that annotations 124 were accurate, and field data 122 itself was unusual. In such embodiments, according to an optional next operation 450, a new grade per the override input is set as the assigned grade, and execution returns to operation 430. The result is that a user signal will be output that encodes the new grade.

Different ways are now described for assigning the grade. Many of these depend on whether the annotations meet accuracy criteria, it will be seen that the notion of not meeting an accuracy criterion can be expressed mathematically as computing the accuracy score, for example as described above with reference to FIG. 5. And, once accuracy scores are computed, the grades cars be letter grades as seen in FIG. 6.

In some embodiments, a flag is issued when at least one aspect of the annotations does not meet an accuracy criterion, and the grade is assigned according to how many flags have been issued. The same can be implemented for two or more accuracy criteria.

In certain implementations, an accuracy criterion can include that there should be no event missing in a series of successive events. These events could be, for example, compressions or ventilations. An example of a missing compression was seen in FIG. 3. In such embodiments, the grade can be an accuracy score that is computed from how many events were identified, and how many were expected to be identified but missed. For example, at the end of a CPR cycle, the accuracy score for the "<c>" annotations can be expressed as: Accuracy Score=100%×[(total<c> counted)−(total<c> missed)/(total<c> counted)].

In a number of embodiments, the annotations include events identified as occurring in sequence at different times. For example, these times would be the ones denoted by the vertical arrows in FIG. 3. Various accuracy criteria can be devised according to these times.

One possible accuracy criterion cars be that there should be no isolated identified event occurring after an idle interval of a first duration, and before another idle interval of a second duration, in other words, the protocol by which rescuer 184 has been trained on may dictate that such events should be occurring only in series. If the annotations include such an isolated event, these annotations were probably generated in error. On the other hand, this may be exactly the kind of unusual field data, perhaps by an error of rescuer 184, which the annotator would override in operation 450 of FIG. 4.

Another possible accuracy criterion can be that identified events should not occur faster than a maximum repetition rate, or slower than a minimum repetition rate. For example, the chest compressions delivered by chest compression machines may be double-counted occasionally. Mathematically, for compressions the rate could be defined as: Repetition rate=(total <c> counted)/(period of time of CPR cycle), the maximum repetition rate can be 150 compressions per minute, and the minimum repetition rate can be 70 compressions per minute. Parallel rules rates can he determined for ventilations.

One more possible accuracy criterion can be that successive events should be taking place at substantially consistent time intervals. More particularly, an average time interval can be determined between the occurrences of two successive events. From this time interval, an expected time interval for the next event can be determined, such as by an algorithm. The accuracy criterion can be that an event should not be followed with a pause in that expected time interval.

The expected time interval can be defined with statistics. For example, in addition to the average time interval, the standard deviation can also be computed. For chest compressions, it should be remembered that compressions may vary substantially based on who is administering them, and so this computation is preferably renewed with every new CPR cycle, as rescuers could be alternating. As such, upon detecting the first<c> after a pause, a running average of the time interval between ail previous compressions and the current compression can be taken, in addition to the standard deviation. For any one<c>, if another<c> is not detected within the running average plus-or-minus three times the standard deviation, it cars be assumed that a compression has been missed. Only 0.2% of a sample population fails outside of a range of plus-or-minus 3 standard deviations, so the confidence in this algorithm is quite high. Such an algorithm would have caught the error in FIG. 3. An upper limit must also be set, in order to detect real pauses in compressions. If there is a pause of more than 1.5 sec between compressions, it should be counted as intended break. There may be user-selectable configuration parameters that modify the sensitivity of the accuracy assessment (such as 2 or 4 standard deviations rather than 3). Furthermore, because compression rates can change within a long CPR interval (i.e. rescuer 184 can become tired), the standard deviation will update in this case, to include only a select window of previous data, as to allow the rate to stay relatively dynamic without being considered inaccurate.

As seen above, in some embodiments, the time interval is tracked by a running average, which could favor the last few events. Of course, a running average and standard deviation computations are necessarily inaccurate for the first few, e.g. five, measurements. This can be overcome by not checking for the first few<c> events as they are identified, but returning to them after the cycle is complete and the end values of average and standard deviation of the cycle have been established.

More criteria can be used, in addition to examining only annotations 124. For example, field data 122 itself can optionally also be examined. In some embodiments, a flag can be further issued, when at least one aspect of field data 122 does not meet one or more validity criteria. Validity criteria can be defined to facilitate the assessment. For example, a validity criterion can be that the field data represents a signal that is larger than a threshold. This can be useful where field data 122 is derived from ECG or impedance signals, and the signals are not much larger than noise.

Figure 8:
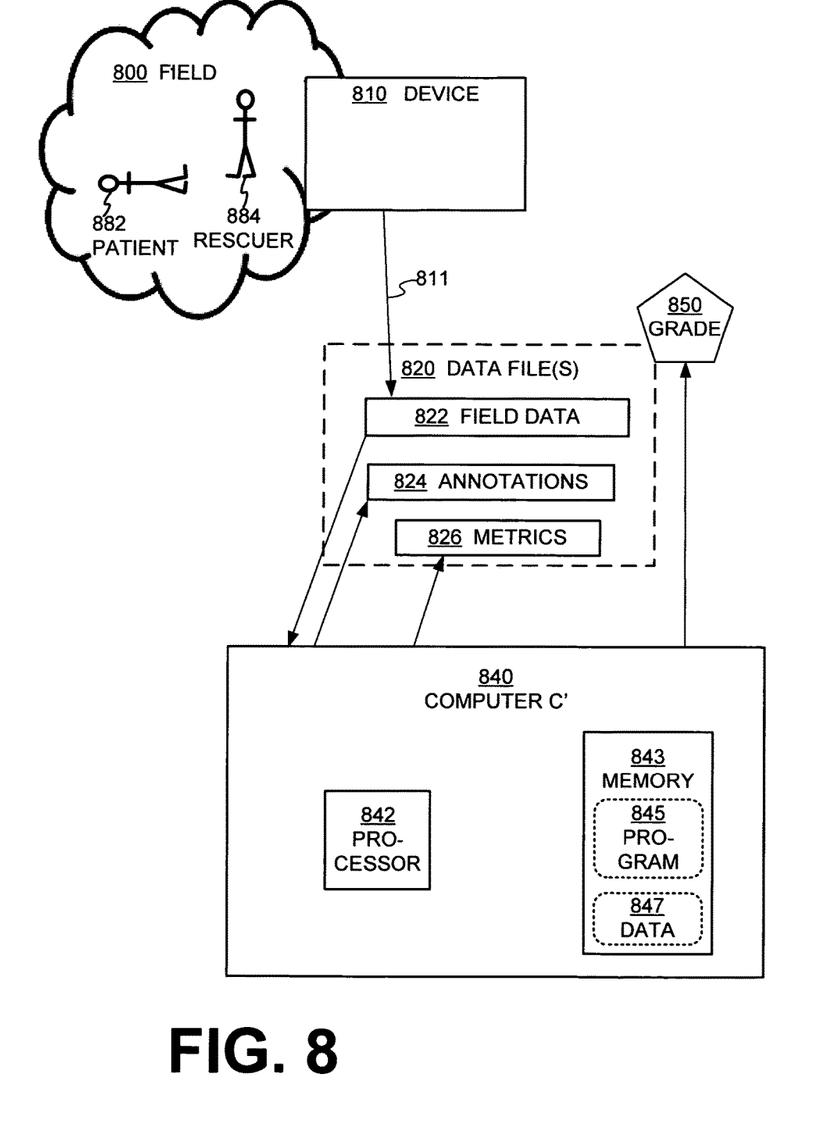
FIG. 8 is another diagram for describing managing data according to embodiments.

FIG. 8 is another diagram for describing managing data according to embodiments. Many of its components are similar to those of FIG. 1. FIG. 8 shows a field 800 where a rescuer 884 could be helping a patient 882. In addition, a device 810 is used, which may be similar to device 110. Device 810 generates field data 822, and may transmit it via arrow 811, similarly with arrow 111. Device 810 may also possibly generate annotations 824.

A Computer C' 840 is also shown. As with FIG. 1, FIG. 8 does not speak to the location of Computer C' 840 relative to field 800. In some embodiments, Computer C' 840 is a remote server to which device 810 can send field data 822 and optionally also annotations 824. In other embodiments, Computer C' 840 could a portable computer that rescuer 884 takes to field 800, such as a tablet computer.

Computer C' 840 has a processor 842 and a memory 843, similarly with what was written above about Computer B' 140. Memory 843 may store a program 845 and data 847. Processor 842 may be able to execute program 845, for performing the operations, algorithms and methods of Computer C' 840.

In many embodiments, Computer C' 840 can perform one or more of the operations shown in FIG. 4. Optionally, it may also generate annotations 824 similar to annotations 124, after receiving field data 822. Further, Computer C' 840 may further generate metrics 826 similar to metrics 126, either from annotations 824 or any annotations received from device 110. Computer C' 840 may further assign a grade 850, similar to grade 150, and output a use signal that encodes assigned grade 850.

Moreover, if Computer C' 840 is implemented as a server in the cloud, it may he capable of performing additional operations, algorithms and methods as some sort of gate keeper. Examples are now described.

Figure 9:
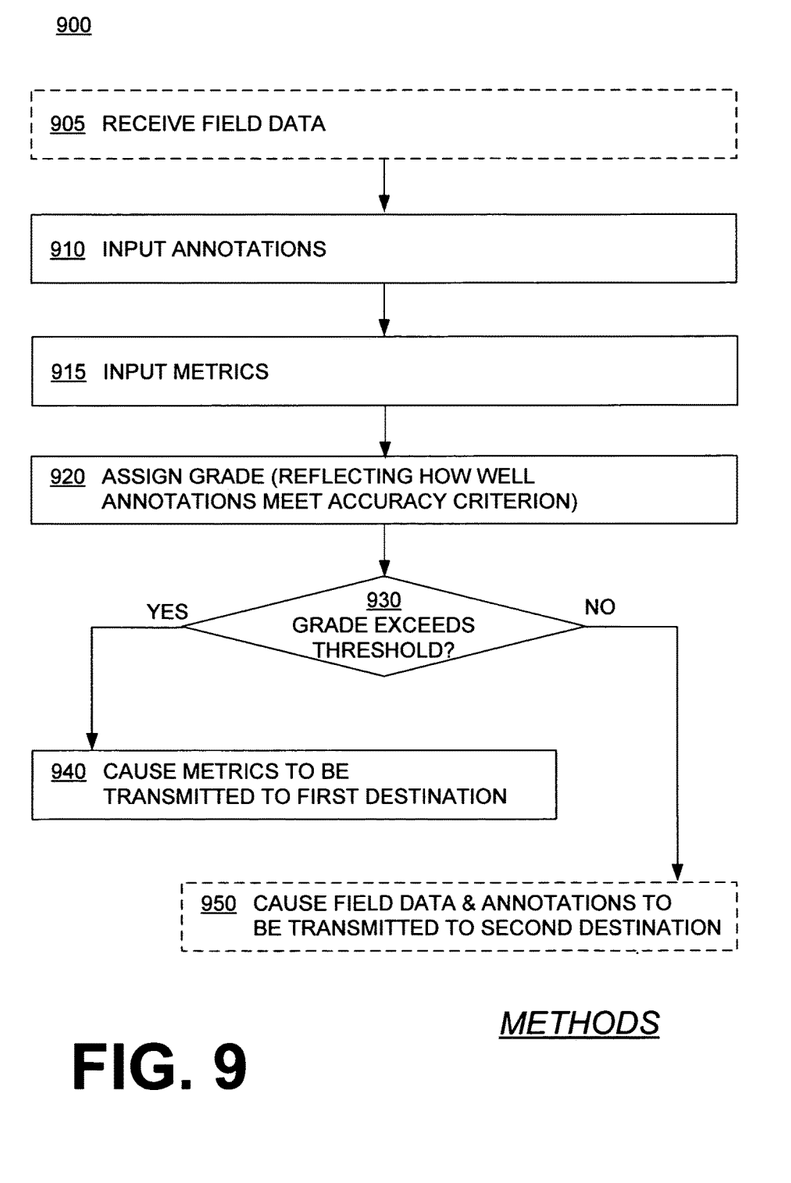
FIG. 9 is a flowchart for illustrating methods according to embodiments.

FIG. 9 shows a flowchart 300 for describing methods according to embodiments. The methods of flowchart 900 may also be practiced by Computer C' 840 and other embodiments.

According to an optional operation 905, field data is received. The field data may be received as data, or measured from a patient, if the functionality is available.

According to an operation 910, annotations are input, which could be performed similarly to operation 410. If the field data has been received, annotations are first generated, and then are input into subsequent operations of this method.

According to another operation 915, metrics are input, which have been determined from the annotations, in some embodiments, the metrics are first computed, and then are input into subsequent operations of this method.

According to a next operation 920, a grade is assigned, which could be performed similarly to operation 420. According to an optional next operation 930, it is inquired whether the grade exceeds a threshold. If so, then according to a next operation 940, the metrics are caused to he transmitted to a first destination, preferably where they would be used for review and training. If not, however, the first destination may not receive the metrics, as part of the gate keeping function. Optionally, according to another operation 950, the field data and annotations may be transmitted to a second destination. The second destination could be an annotator.

There can be variations in the above. The threshold, or one of the destinations, may be adjusted, if an appropriate input is received, for example by a user.

Figure 10:
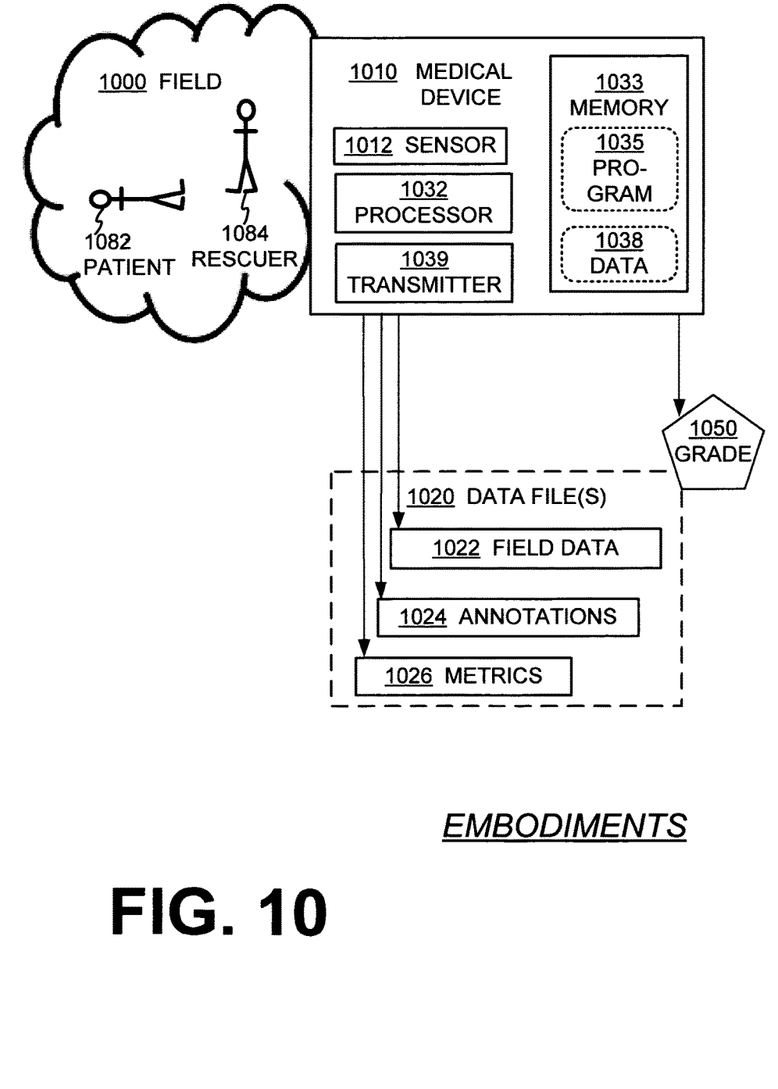
FIG. 10 is a diagram for illustrating use of a medical device according to embodiments.

FIG. 10 is a diagram for illustrating use of a medical device 1010 according to embodiments. Device 1010 is used in field 1000 by a rescuer 1084 who is tending to patient 1082.

Device 1010 includes a sensor 1012 that can be as sensor 112. Sensor 1012 may sense field data 1022 from the patient, such as a physiological parameter, a chest height, and so on.

Device 1010 may also include a processor 1032 and a memory 1033. Memory 1033 may store a program 1035 and data 1038. Processor 1032 may execute program 1035. When it does, in some embodiments, the results include that annotations 1024 are generated from field data 1022. The annotations could purport to identify events within the field data. The results could further include assigning a grade 1050 that, reflects how well annotations 1024 meet at least one accuracy criterion, such as described above.

Device 1010 may additionally include a transmitter 1039. Transmitter 1039 may be able to transmit a wireless output signal that encodes the assigned grade. The wireless output signal may further encode field data 1022 and/or annotations 1024. In some embodiments, executing the program further results in computing metrics 1026 from annotations 1024. In some of those embodiments, the wireless signal further encodes the metrics.

In addition, device 1010 is capable of performing previously described processes, operations, algorithms and methods. Moreover, in some embodiments, device 1010 is a learning device. In other words, it learns from the grade if assigns, and adjusts its parameters for generating annotations, so as to improve the grade. Accordingly, the grade may be used internally, and might never even be transmitted out of the device. Examples are now described.

Figure 11:
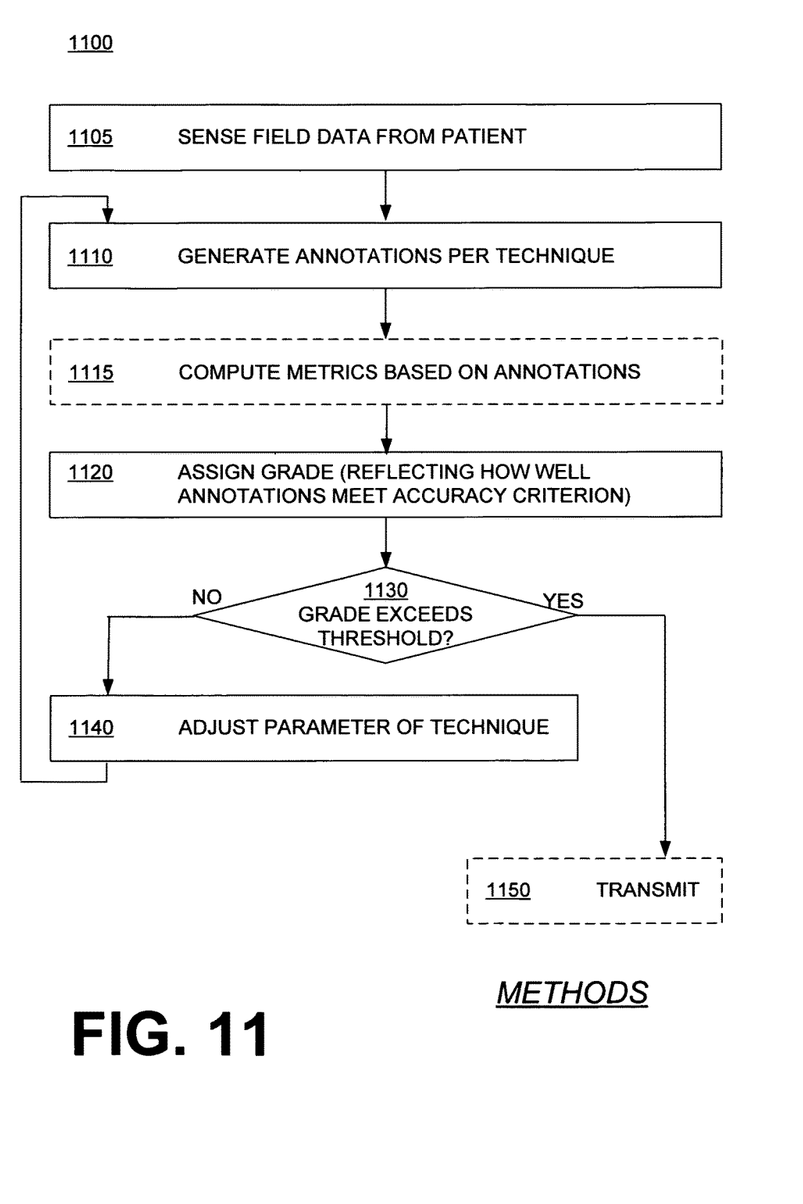
FIG. 11 is a flowchart for illustrating methods according to embodiments of the invention.

FIG. 11 shows a flowchart 1100 for describing methods according to embodiments. The methods of flowchart 1100 may also be practiced by embodiments described above. According to an operation 1105, field data is sensed from a patient, such as by using sensor 1012. According to another operation 1110, annotations are generated from the field data. Generation can be according to a technique that uses a parameter. The parameter can be a mathematical parameter that is used as a trigger for identifying the events within the field data. According to an optional operation 1115, metrics are computed based on the annotations. According to another operation 1120, a grade is assigned, as has been described above.

According to another operation 1130, it is inquired whether the assigned grade exceeds a threshold, if not, then according to operation 1140, the parameter is adjusted, and execution returns to operation 1110. When execution then reaches operation 1130 again, the updated grade may exceed the threshold.

If, at operation 1130 the grade exceeds the threshold, then according to an optional next operation 1150, there is transmitting of any one or more of the field data, the annotations and the metrics. The grade need not be transmitted, but it may.

The methods of flowchart 1100 can further be augmented with techniques for adjusting the threshold, so that the search for the best result does not take undue amounts of time. In some embodiments, operation 1115 is moved out of the loop, until a satisfactory grade is found.

In the methods described above, each operation can be performed as an affirmative step of doing, or causing to happen, what is written that can take place. Such doing or causing to happen can be by the whole system or device, or just one or more components of it. In addition, the order of operations is not constrained to what is shown, and different orders may be possible according to different embodiments. Moreover, in certain embodiments, new operations may be added, or individual operations may be modified or deleted. The added operations can be, for example, from what is mentioned while primarily describing a different system, device or method.

This description includes one or more examples, but that does not limit how the invention may be practiced. Indeed, examples or embodiments of the invention may be practiced according to what is described, or yet differently, and also in conjunction with other present or future technologies.

A person skilled in the art will be able to practice the present invention in view of this description, which is to be taken as a whole. Details have been included to provide a thorough understanding. In other instances, well-known aspects have not been described, in order to not obscure unnecessarily the present invention.

Other embodiments include combinations and sub-combinations of features described herein, including for example, embodiments that are equivalent to: providing or applying a feature in a different order than in a described embodiment, extracting an individual feature from one embodiment and inserting such feature into another embodiment; removing one or more features from an embodiment; or both removing a feature from an embodiment and adding a feature extracted from another embodiment, while providing the advantages of the features incorporated in such combinations and sub-combinations.

The following claims define certain combinations and subcombinations of elements, features and steps or operations, which are regarded as novel and non-obvious. Additional claims for other such combinations and subcombinations may be presented in this or a related document.

What is claimed is:

1. A device comprising:
   a processor; and
   a non-transitory storage medium communicatively coupled to the processor, the storage medium configured to store one or more programs which, when executed by the processor, cause the device to:
   receive field data, derived from a Cardio Pulmonary Resuscitation (CPR) session, including events of at least two different types occurring to a patient over time, the event types including at least one of chest compressions and ventilations within the CPR session;
   receive annotations that have been previously generated from field data, the annotations identifying at least some of the events;
   calculate at least one of a relative timing of at least two events of the field data based on the annotations identifying the at least two events;
   obtain at least one accuracy criterion, the accuracy criterion indicating an expected event sequence and the relative timing of the at least two events;
   compute at least one accuracy score for the annotations based on the accuracy criterion;
   assign, out of a plurality of possible grades, at least one grade based on the accuracy score, the assigned grade indicating an accuracy with which the annotations identify the events identified by the annotations, and
   output a user signal that includes the at least one grade for the annotations.

2. The device of claim 1, in which
the field data is arranged along a time dimension, and
the annotations include events identified as occurring in sequence at different times along the time dimension.

3. The device of claim 1, in which
the events result in repeating patterns within the field data.

4. The device of claim 1, in which
assigning the at least one grade is accomplished by selecting one of a plurality of bands with boundaries that contain the accuracy score, and assigning a grade corresponding to the selected band.

5. The device of claim 1, in which
the grade is encoded to be heard with a sound different than respective sounds of the other possible grades.

6. The device of claim 1, in which
the grade is encoded to appear with a color or an image different than respective colors or images of the other possible grades.

7. The device of claim 1, in which
the user signal also includes, in association with the grade, metrics that are computed from the annotations.

8. The device of claim 1, in which executing the one or more programs further causes the device to:
receive adjusted annotations generated from the field data after the annotations;
assign an adjusted grade reflecting an accuracy with which the adjusted annotations identify events in the field data based on the accuracy criterion; and
output a user signal that encodes the adjusted grade.

9. The device of claim 1, in which executing the one or more
programs further causes the device to:
   receive an override input; and
   output a user signal that encodes a new grade different from the assigned grade responsive to receiving the override input.

10. The device of claim 1, in which
a flag is issued when at least one aspect of the annotations does not meet the at least one accuracy criterion, and
the grade is assigned based on a number of issued flags.

11. The device of claim 10, in which
a flag is issued when at least one aspect of the annotations does not meet a plurality of accuracy criteria.

12. The device of claim 10, in which
the at least one accuracy criterion specifies that no event is missing in a series of successive events.

13. The device of claim 12, in which
the grade and the accuracy score are computed based on a number of identified events and a number of expected events.

14. The device of claim 10, in which
the annotations include events identified as occurring in sequence at different times, and
the at least one accuracy criterion specifies that no isolated identified event occurs after an idle interval of a first duration and before another idle interval of a second duration.

15. The device of claim 10, in which
the annotations include events identified as occurring in sequence at different times, and
the at least one accuracy criterion specifies that identified events do not occur faster than a maximum repetition rate, or slower than a minimum repetition rate.

16. The device of claim 10, in which
the annotations include events identified as occurring in sequence at different times,
an average time interval between the occurrences of two successive events is determined, and
the at least one accuracy criterion specifies that an event should be followed with a pause in an expected time interval that is determined by the average time interval.

17. The device of claim 10, in which
a flag is further issued when at least one aspect of the field data does not meet at least one validity criterion.

18. The device of claim 17, in which
the at least one validity criterion specifies that the field data represents a signal that is larger than a threshold.

19. A method comprising:
receiving field, derived from a Cardio Pulmonary Resuscitation (CPR) session, including events of at least two different types occurring to a patient over time, the event types including at least one of chest compressions and ventilations within the CPR session;
receiving annotations that have been previously generated from field data, the annotations identifying at least some of the events;
calculate at least one of a relative timing of at least two events of the field data based on the annotations identifying the at least two events;
obtain at least one accuracy criterion, the accuracy criterion indicating an expected event sequence and the relative timing of the at least two events;
computing at least one accuracy score for the annotations based on the accuracy criterion;
assigning, out of a plurality of possible grades, at least one grade based on the accuracy score, the assigned grade indicating an accuracy with which the annotations identify events identified by the annotations; and
outputting a user signal that includes the at least one grade for the annotations.

20. A non-transitory computer-readable storage medium storing one or more programs which, when executed by at least one device, they result in:
receiving field data, derived from a Cardin Pulmonary Resuscitation (CPR) session, including events occurring to a patient over time, the events including at least one of chest compressions and ventilations within the CPR session;
receiving annotations that have been previously generated from field data, the annotations identifying at least some of the events;
calculate at least one of a relative timing of at least two events of the field data based on the annotations identifying the at least two events;
obtain at least one accuracy criterion, the accuracy criterion indicating an expected event sequence and the relative timing of the at least two events;
assigning, out of a plurality of possible grades, at least one grade for the annotations based on the accuracy criterion by comparing the field data associated with the annotations with the expected event sequence, the assigned grade indicating an accuracy with which the annotations identify events identified by the annotations; and
outputting a user signal that encodes the grade.

21. A medical device, comprising:
a sensor configured to sense one or more patient parameters used to sense field data about a patient, the field data derived from a Cardio Pulmonary Resuscitation (CPR) session and including events occurring to the patient over time, the events including at least one of chest compressions and ventilations within the CPR session;
a processor;
a non-transitory memory configured to store one or more programs which, when executed cause the medical device to:
generate annotations from the field data, the annotations identifying one or more events within the field data,
obtain at least one accuracy criterion indicating an expected order of an event sequence,
compute at least one accuracy score for the annotations based on the accuracy criterion, and
assign, out of a plurality of possible grades, at least one grade based on the accuracy score, the assigned grade indicating an accuracy with which the annotations identify the events; and
a transmitter for transmitting a wireless output signal that includes the at least one grade for the annotations.

22. The medical device of claim 21, in which the execution of the one or more programs further cause the medical device to:
compare the at least one grade to a threshold,
adjust at least one parameter used to generate at least one of the annotations when the grade does not meet the threshold,
generate adjusted annotations based on the adjusted parameter, and assign at least one adjusted grade to the adjusted annotations for inclusion in the wireless output signal.

23. The device of claim 1, further comprising an output device including a user interface, in which, responsive to the user signal, outputs a human perceptible indication that conveys the grade.

* * * * *